United States Patent [19]
Euzen et al.

[11] Patent Number: 5,869,541
[45] Date of Patent: Feb. 9, 1999

[54] CONVERSION OF SYNTHESIS GAS TO HYDROCARBONS IN THE PRESENCE OF A LIQUID PHASE

[75] Inventors: Jean-Paul Euzen, Dardilly; Isabelle Harter, Lyons; Patrick Chaumette, Bougival, all of France

[73] Assignees: Institut Francais du Petrole, France; AGIP Petroli S.p.A., Italy

[21] Appl. No.: 815,987

[22] Filed: Mar. 10, 1997

[30] Foreign Application Priority Data

Mar. 8, 1996 [FR] France ................................ 96 02911

[51] Int. Cl.⁶ .................................................. C07C 27/00
[52] U.S. Cl. ............................................................ 518/700
[58] Field of Search ............................................. 518/700

[56] References Cited

U.S. PATENT DOCUMENTS

| | | | |
|---|---|---|---|
| 5,037,856 | 8/1991 | Post et al. | 518/714 |
| 5,232,283 | 8/1993 | Goebel et al. | 366/336 |

FOREIGN PATENT DOCUMENTS

| | | |
|---|---|---|
| 0 188 304 | 7/1986 | European Pat. Off. . |
| 0 212 202 | 3/1987 | European Pat. Off. . |
| 897 549 | 10/1953 | Germany . |
| 7708307 | 1/1979 | Netherlands . |
| 728 543 | 4/1955 | United Kingdom . |

*Primary Examiner*—Gary Geist
*Assistant Examiner*—Jafar Parsa
*Attorney, Agent, or Firm*—Millen, White, Zelano, & Branigan, P.C.

[57] ABSTRACT

A process for the synthesis of essentially linear saturated $C_5^+$ hydrocarbons from a gas phase comprising synthesis gas is described. The process comprises circulation of an inert liquid phase and said gas phase in a reaction zone, in which the reaction zone is provided with at least one means for introducing gas and liquid phases, and at least one means for extracting the hydrocarbon phase formed by the Fischer-Tropsch reaction, and characterized in that the reaction zone comprises at least one mixing means. Preferably, at least one mixing means is a static mixer. An apparatus for carrying out the described process is also described.

26 Claims, 3 Drawing Sheets

CONVERSION OF SYNTHESIS GAS TO HYDROCARBONS IN THE PRESENCE OF A LIQUID PHASE

The present invention concerns a process for the synthesis of essentially $C_5^+$ hydrocarbons (i.e., hydrocarbons containing at least 5 carbon atoms per molecule) from synthesis gas, for use as motor fuel or liquid fuel.

Synthesis gas is a $CO$—$(CO_2)$—$H_2$ mixture, i.e., a $CO$—$H_2$ mixture of carbon monoxide (CO) and hydrogen ($H_2$) which may contain carbon dioxide ($CO_2$). The synthesis of hydrocarbons from synthesis gas, generally carried out at a temperature which is in the range 150° C. to 350° C. and under pressure, is known as the Fischer-Tropsch synthesis. The catalysts which are normally used for transformation of $CO$—$(CO_2)$—$H_2$ mixtures to liquid or gaseous hydrocarbons generally comprise at least one metal from group VIII such as iron, ruthenium, cobalt or nickel.

The products prepared by the Fischer-Tropsch synthesis in the presence of these metallic catalysts have a very wide molecular weight distribution. The reaction which is of interest in the present application is the synthesis of essentially $C_5^+$ hydrocarbons from synthesis gas.

The Fischer-Tropsch synthesis is a highly exothermic reaction. So much so, that when the process for carrying out this synthesis reaction is operated in the gas phase with a fixed bed catalyst, the conversion of carbon monoxide must be limited to less than 85% to avoid thermal instabilities in the catalytic bed, which means that the unconverted synthesis gas must be separated and recycled.

Another process which has been envisaged for carrying out the reaction is conducted in the presence of a liquid phase and with the catalyst in suspension (a circulating bed reactor, also known as a slurry reactor). In this case, CO conversion can reach and even exceed 95%. However, the catalyst which is taken up into suspension and circulated with the inert liquid must be separated from the reaction products then recycled.

A further process which has been envisaged consists of operating in the presence of a liquid phase, mixed with the synthesis gas, and with a fixed bed catalyst. Thus United States patent U.S. Pat. No. 4,413,063 and French patent application 95/08 637 dated 13 Jul. 1995 describe processes which can synthesize hydrocarbons or alcohols from synthesis gas in the presence of a catalyst and an inert diluent, the synthesis gas and the liquid phase circulating downwards (respectively upwards) through the fixed bed catalyst. The fixed bed reaction zone with a descending or ascending flow of liquid and gas is also known as a "trickle bed" and is a solution which avoids the circulation and separation of the catalyst while limiting thermal instabilities.

For the Fischer-Tropsch synthesis, the use of a trickle bed type reactor can, however, lead to a degradation in the activity and/or selectivity towards $C_5^+$ hydrocarbons. This degradation is very important when the fluids flow from top to bottom in a dropper reactor. In this case, the degradation is more important when the surface velocity of the liquid phase is low and that of the gas phase is high. This problem greatly limits the possibilities for industrial development of a trickle bed type reactor since, for a given conversion, in order to eliminate the heat produced by the reaction and have sufficient catalytic performances, very large reactors are required in order to be able to operate at reasonable fluid circulation rates, meaning that they are relatively expensive and difficult to use.

The same is true for the other types of reactors operating in the presence of a liquid phase and a catalyst in suspension (slurry type reactors or ebullated bed reactors).

Without wishing to be tied to a particular theory, it appears that this degradation of reactor performances is due, at least in part, to problems of distribution and segregation of fluids which are the gas and liquid phases, which cause a portion of the liquid to be in contact with the catalyst under conditions such that the quantity of synthesis gas present in that region is too high or too low to ensure optimal selectivity and conversion in the Fischer-Tropsch synthesis reaction.

The problem is thus to find a means or method which, for a given conversion, can produce good performances as regards activity and selectivity towards $C_5^+$ hydrocarbons.

The present invention provides a solution to this problem which can improve the activity and selectivity of the Fischer-Tropsch synthesis reaction.

The present invention thus provides a means which can mix the liquid and gas phases, to allow homogeneous distribution of said phases before contact with the catalyst bed (and preferably before each bed) in the case of a trickle bed reactor, or in the liquid phase containing the suspended catalyst in the case of a slurry type reactor or an ebullated bed type reactor.

More precisely, the present invention concerns a process for the synthesis of essentially linear saturated $C_5^+$ hydrocarbons from a gas phase comprising synthesis gas, comprising circulation of a liquid phase and said gas phase in a reaction zone, in which the reaction zone is provided with at least one means for introducing gas and liquid phases, and at least one, preferably only one, means for extracting a hydrocarbon phase formed by the Fischer-Tropsch reaction, and characterized in that the reaction zone comprises at least one mixing means.

The mixing means is thus generally located upstream of the extraction means, preferably upstream of the only extraction means.

In one implementation of the process of the invention, at least one mixing means is also a distribution or redistribution means for the liquid and gas phases.

In a further implementation of the process of the invention, which may or may not be independent of the preceding implementations, at least one mixing means is associated with a means for distribution or redistribution of the liquid and gas phases.

In a further implementation of the process of the invention, which may or may not be independent of the preceding implementation, at least one mixing means is located in the means for introducing the gas and liquid phases.

The process of the invention is preferably such that at least one, preferably each mixing means is a static mixer, selected from static mixers which are well known to the skilled person. As a non limiting example of a static mixer, one described and sold by SULZER could be used, for example those with reference SMV or SMX, described in the review "Chemical Engineering Progress", Vol. 75, No. 4, April 1979, pages 61 to 65. A further type of static mixer is described in EP-B-0 212 202. Further descriptions of static mixers which could be used in process of the present invention are given in the book "les réacteurs chimiques, conception, calcul et mise en oeuvre" [Chemical reactors: design, engineering and operation] published by TECHNIP in 1984, particularly pages 599 to 605. Such a static mixer is composed, for example, of plates disposed at a certain angle and arranged so as to form open channels which cross over, disposed obliquely with respect to the reaction zone axis.

In the present invention, the liquid phase and the synthesis gas circulate in a reaction zone containing either at least one fixed catalytic bed comprising a catalyst in the form of a divided solid (trickle bed type), or particles of catalyst in suspension in the liquid phase (slurry or ebullated bed type).

The catalyst particles generally have an average diameter (equivalent diameter) which is in the range 0.2 to 10 mm, preferably in the range 0.5 to 6 mm and more preferably in the range 1 to 3 mm, in the case of a trickle bed, and in the range 30 to 300 μm, preferably in the range 50 to 100 μm, in the case of a slurry type process, and in the range 100 and 5000, preferably in the range 0.35 to 3 mnm, in the case of an ebullated bed type process.

In one implementation of the process of the invention, said process is a trickle bed. In such a case, the process is preferably such that the reaction zone comprises at least one catalytic bed, and such that the liquid and gas phases circulate in the same direction, and the process is characterized in that at least one, preferably each, catalytic bed is associated with at least one mixing means, located upstream of said catalytic bed, in the sense of the passage of said phases over said bed. Preferably, one implementation of the process of the invention is such that at least one mixing means located between two catalytic beds is associated upstream with a means for collecting the liquid and gas phases and downstream with a means for redistributing the liquid and gas phases. In a further implementation of the process of the invention, which may or may not be independent of the preceding implementation, at least one mixing means located between two catalytic beds is also a means for collecting liquid and gas phases arriving from upstream and a means for redistributing the liquid and gas phases in a downstream direction. When the process is a trickle bed type process, whatever the embodiment used, at least one mixing means is a static mixer and said mixer comprises at least a portion, or the totality, of the catalyst present in the catalytic bed with which said mixer is associated.

When the reactor used is a trickle bed type reactor, and at least one mixing means is a static mixer, a plurality of static mixers can be used simultaneously and disposed in accordance with one of the implementations described above. When the static mixer is not immediately upstream of the catalyst bed (or of the bed of non catalytic solid particles if the catalyst bed is preceded by such a solid particle bed), a distribution or redistribution means is usually disposed upstream of the bed, consisting, for example, of a conventional distribution plate such as one of those described on p 308 or p 490 of the TECHNIP publication cited above. This distribution plate can be upstream or downstream of a static mixer. When the static mixer is immediately upstream of the solid particle bed, a fluid distributor alone is used only if the static mixer cannot act as a distributor at the same time.

The liquid phase does not take part in the reaction and has no deleterious effect on the latter. It is preferably a hydrocarbon cut, more preferably containing essentially 10 to 20 carbon atoms per molecule, such as a gas oil cut or a kerosine cut, the kerosine fraction(s) being constituted by a mixture of hydrocarbons with boiling points which are approximately in the range 140° C. to 300° C., and the gas oil fraction(s) being constituted by a mixture of hydrocarbons with boiling points which are approximately in the range 180° C. to 370° C. during atmospheric distillation as carried out on a crude oil by a skilled person. If the catalyst is sensitive to sulphur, a desulphurized hydrocarbon cut is preferably used.

In a preferred implementation of the process of the invention, the liquid phase comprises at least one partially vaporizable product, for example 0 to 80% of an at least partially vaporizable product. This improves the evacuation of heat and heat transfer in the reaction zone. The term "vaporizable" means any liquid product which, under the reaction conditions, is practically completely in the gas form. The term "partially vaporizable product" means a product of which a portion, generally between 10% and 100%, is vaporizable. In the present implementation of the invention, the liquid phase preferably comprises a partially vaporizable hydrocarbon cut, for example a hydrocarbon cut comprising hydrocarbons containing 5, 6, 7, 8, 9 or 10 carbon atoms per molecule.

In a preferred implementation of the invention, which may or may not be independent of the preceding implementation, the inert liquid phase is advantageously obtained by recycling a portion of a hydrocarbon fraction produced by the reaction; preferably, said fraction is a gas oil or kerosine fraction of the hydrocarbons produced by the reaction. In this case, the inert liquid phase which is initially introduced into the reaction zone is brought outside (in contrast to a liquid phase produced in the Fischer-Tropsch reaction zone, i.e., inside), by which time said liquid phase comprises a portion of a hydrocarbon fraction produced by the reaction which is recycled to said zone. Said fraction is preferably the gas oil or kerosine fraction.

By way of indication, the inert liquid phase generally has a density which is in the range 0.2 to 2.5 $g/cm^3$ and a viscosity which is in the range 0.05 to 10 centipoises (0.05 to 10 mPa.s) under the reaction conditions, but these values are not compulsory.

With trickle bed reactors, the reaction zone usually consists of a reactor which is elongate along one axis, with a cross section which can be of any shape but is usually square, rectangular or circular. A reactor with a circular cross section is normally used which also comprises an inlet conduit opening into the reactor, normally such that the fluids are introduced in the direction of the reactor axis, and an outlet conduit which is normally oriented, at least in the immediate proximity of the reactor, along the axis of the reactor. The reactor diameters are generally of the order of 0.05 m to 7 m, preferably 0.1 m to 2.5 m.

In an advantageous implementation of the invention, the reaction zone in a trickle bed type process consists of a reactor which contains a plurality of fixed beds each containing a catalyst for the Fischer-Tropsch reaction, which may be identical or different from one bed to another, separated from each other by at least one mixing means which can collect the liquid and gas phases leaving a fixed catalyst bed, mix the collected phases, and redistribute the mixture to the fixed catalyst bed located downstream in the overall circulation direction of said fluids in the reactor. When the reactor contains a plurality of catalytic beds, it is particularly advantageous if at least one, preferably each mixing means which collects fluids, mixes them and redistributes them further comprises at least one means for introducing synthesis gas into the collected mixture.

Remaining with this implementation of the process of the invention, the mixing means located between two catalyst beds and collecting, mixing and redistributing the liquid and gas phases can be a static mixer which can carry out all of these functions. The use of a static mixer which does not redistribute the fluids and adding a conventional distributor does not go beyond the scope of the invention. In particularly preferred fashion, the static mixer(s) thus located in the trickle bed type reactor occupy the whole of the reactor cross section or, more precisely, the mixer covers a cross section which is at least equal to that of the upstream bed and/or at least equal to that of the downstream bed (except for the mixer located upstream of the first catalytic bed, generally in the reactor inlet conduit). In this way, the velocities in the bed(s) and mixer(s) are substantially identical. All combinations of the described variations are possible. The process of the present invention is applicable when the liquid phase and the synthesis gas circulates from top to bottom in the reactor, and when one or the other or both of the two fluids circulates from bottom to top.

The process of the invention is particularly suitable for use as a process for the production, from synthesis gas, of a mixture of essentially linear and saturated hydrocarbons, generally containing at least 80% by weight with respect to the totality of the hydrocarbons formed of a cut comprising $C_5^+$ hydrocarbons, and preferably less than 10% by weight of olefins in said $C_5^+$ cut. The process of the invention can thus produce essentially paraffinic hydrocarbons, the fraction with the highest boiling points being converted with a high yield to middle distillates (gas oil and kerosine cuts) by a hydroconversion process such as (catalytic) hydrocracking and/or catalytic hydroisomerisation.

The operating conditions under which the reaction is carried out depend on the nature of the catalyst and are generally as follows.

The conversion of synthesis gas to hydrocarbons is generally operated at a total pressure which is in the range 0.1 to 15 MPa, preferably 0.5 to 10 MPa, the temperature being in the range 150° C. to 350° C., preferably in the range 180° C. to 270° C.

The hourly space velocity is normally in the range 100 to 20000 volumes of synthesis gas per volume of catalyst per hour, preferably in the range 400 to 10000 volumes of synthesis gas per volume of catalyst per hour.

The $H_2/CO$ molar ratio in the synthesis gas is generally in the range 0.5 to 5, preferably in the range 1.2 to 3.5. The $CO_2$ content in the synthesis gas is generally less than 10% by volume.

The process of the invention is operated by first loading the catalyst into the reaction zone, and reducing it by bringing it into contact with at least one reducing compound, for example pure hydrogen or a mixture of reducing gases such as hydrogen and/or carbon monoxide, and optionally at least one inert gas such as nitrogen, the molar ratio (reducing compound):(reducing compound+inert gas) being in the range 0.001:1 to 100:1 when at least one inert gas is present. Reduction is generally carried out between 150° C. and 600° C., preferably between 200° C. and 500° C., between 0.1 and 10 MPa, and at an hourly space velocity of 100 to 40000 volumes of mixture per volume of catalyst per hour. Reduction is optionally carried out in the liquid phase, the liquid phase for reduction being constituted, for example, by at least one hydrocarbon containing at least 5 carbon atoms per molecule.

The invention also concerns an apparatus for carrying out the process as described above.

The apparatus comprises at least one means for circulating a liquid phase and a gas phase in a reaction zone provided with at least one means for introducing gas and liquid phases, and at least one means for extracting the reaction product, said apparatus being characterized in that the reaction zone also comprises at least one means for mixing the gas and liquid phases present.

DETAILED DESCRIPTION OF THE DRAWINGS

Figure 1:
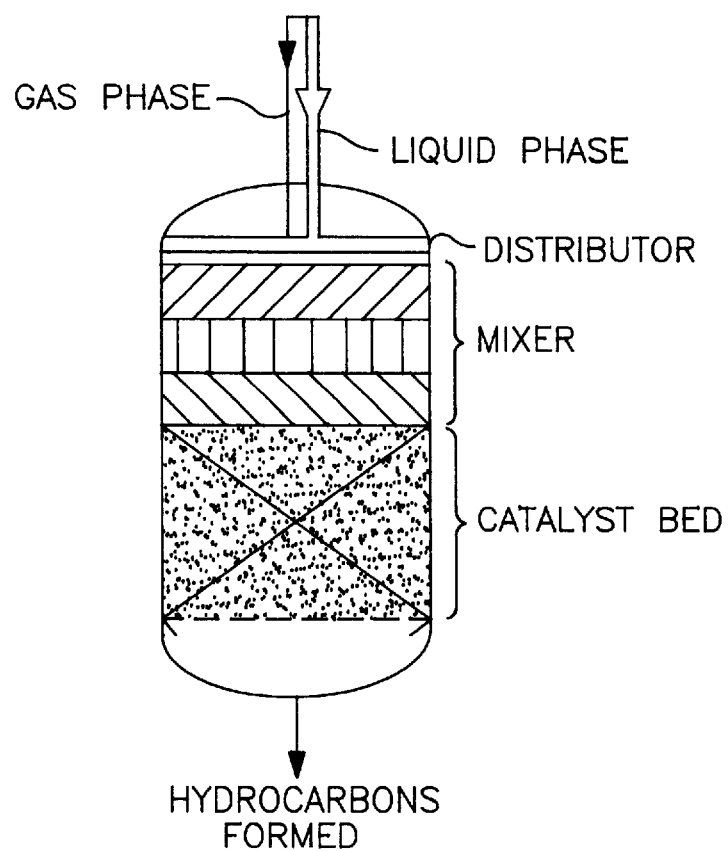
FIGS. 1, 2 and 3 are self-explanatory preferred embodiments of the apparatus of the Invention.
Figure 2:
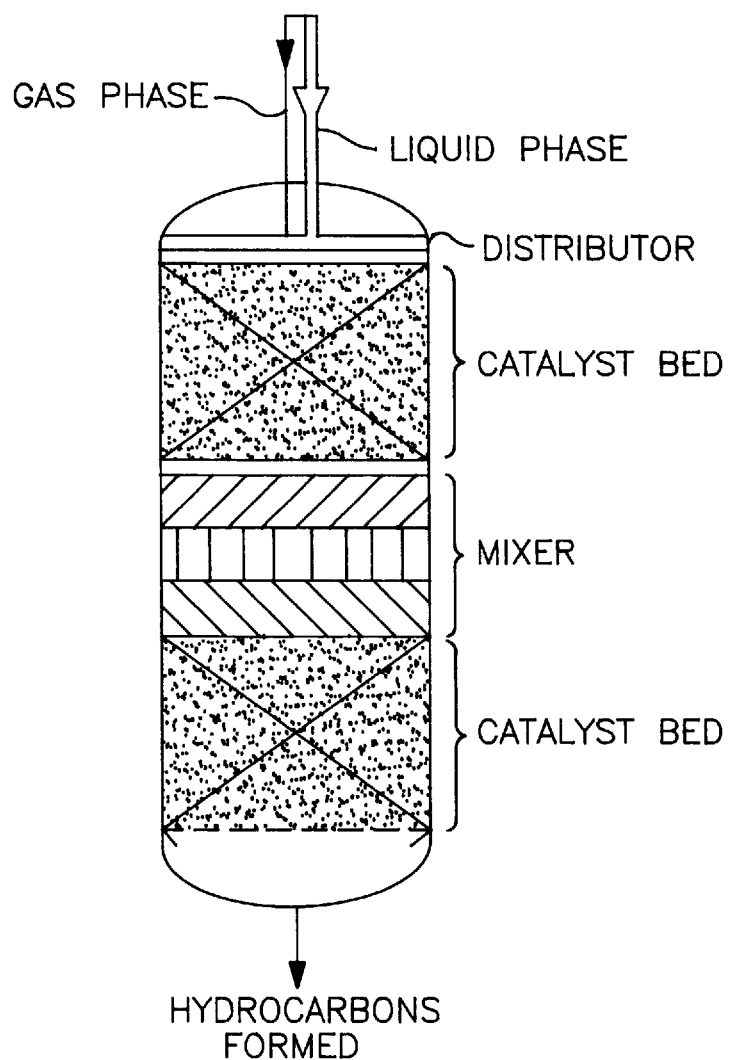
Figure 3:
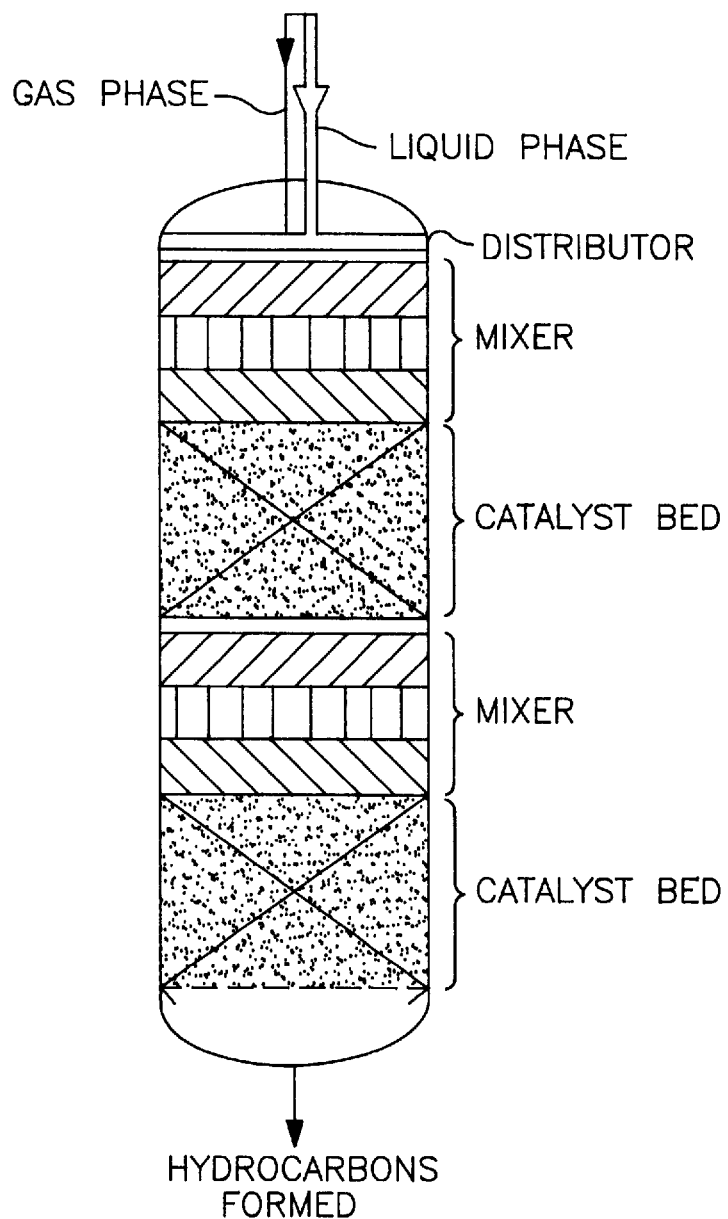

In FIG. 1, there is shown a single catalyst bed and a single static mixer whereas in FIG. 2 two catalyst beds are employed, one upstream and one downstream of the mixer. FIG. 3 depicts an apparatus comprising two mixers and two catalyst beds. With respect to the details of preferred static mixers that can be employed, attention is invited to the description of the same supra, in Chemical Engineering Progress, Vol. 74, No. 4, April 1979, pp. 61–65, as well as in EP-B-0212202 and the text "les reacteurs chimique, conception, cacul and et mise en oeuvre," pp. 599–605.

The following examples illustrate the invention without in any way limiting its scope.

EXAMPLES

The catalyst used in Examples 1 to 4 was prepared as follows:

75 g of a colloidal solution of silica containing 40% by weight of $SiO_2$ (Ludox 40) and 2 ml of 10% nitric acid were simultaneously and slowly added to a solution containing 40 g of cobalt nitrate, 1 g of ruthenium hexamine trichloride and 0.3 g of trihydrated copper nitrate dissolved in 50 ml of water, maintaining the pH between 1 and 2. The solution was left without stirring for 10 minutes; then 25 g of LUDOX AS40 was added, and the pH developed and stabilized at a pH of 5.5 to 6.5. After 12 minutes, a silica gel containing the salts of cobalt, copper and ruthenium was formed.

The gel obtained was separated from the mother liquor by filtering, washing with water, oven drying between 40° C. and 120° C., then calcining at 450° C. followed by forming by pelletizing. The 5×5 mm pellets were then calcined once again at 600° C.

The catalyst was reduced in the reactor, prior to hydrocarbon synthesis, using a mixture containing 6% of hydrogen in nitrogen, up to 240° C., then by pure hydrogen up to 500° C., at atmospheric pressure.

Example 1

(comparative)

In this example, the synthesis gas ($H_2+CO+CO_2$ mixture) and the liquid phase circulated from top to bottom and passed through 12 $dm^3$ of catalyst.

The catalyst above was charged into a reactor which was elongate along a vertical axis, and had a circular cross section and a diameter of 10 cm. The synthesis gas used for the hydrocarbon synthesis consisted of a mixture containing 66.7% of hydrogen and 33.3% of carbon monoxide. The gas was introduced at a flow rate of 12 $m^3/h$, i.e., a GHSV (gas hourly space velocity) of 1000 $h^-$. The reaction was carried out at 220° C. and 2 MPa.

The liquid phase was a $C_{10}$–$C_{16}$ paraffinic cut which contained no sulphur which was introduced at start-up, then separated from the effluents at the reactor outlet and recycled. The flow rate of this liquid phase was about 200 l/h at the reaction temperature, i.e., a space velocity of 4.5 cm/s. The products which were lighter or heavier than this liquid phase, also the water which was co-produced in the reaction, were separated, evacuated and analyzed.

Let the number of gram-molecules of carbon monoxide CO and carbon dioxide $CO_2$ (if $CO_2$ is present) which are transformed into hydrocarbons containing 1 to n carbon atoms per molecule be numbered C1, C2, C3, ... Cn. Then the number Nc of gram-atoms of carbon in the products formed during the reaction is calculated using the following formula:

$$Nc = C1 + 2C2 + 3C3 + \ldots + nCn$$

Thus:

the conversion is defined as the ratio between the number Nc and the number of moles of CO and $CO_2$ (if $CO_2$ is present) in the feed, said ratio being expressed as a percentage;

the selectivity towards methane is defined as the ratio between the number C1 and the number Nc, said ratio being expressed as a percentage;

the selectivity towards $C_5^+$ is defined as the ratio between (5C5+6C6+. . . +nCn) and Nc, said ratio being expressed as a percentage.

Under these conditions, in Example 1, the conversion was 72%, the methane selectivity was 8%, and the $C_5^+$ hydrocarbon selectivity was 86% (see Table 1).

Example 2

(in accordance with the invention)

The same reactor as that of Example 1 was used, with the same operating conditions, and the same catalyst in an identical quantity, but the reactor contained two catalytic beds separated by a SMV type static mixer sold by SULZER, immediately above which was a liquid distributor. The static mixer was formed by three successive plates offset by 90 degrees to each other as described in the Review Chemical Engineering Progress, Vol. 75, No. 4, April 1979, pages 61 to 65. Each plate was 10 cm high.

Under these conditions, conversion was 78%, the methane selectivity was 6%, and the selectivity towards $C_5^+$ hydrocarbons was 88% (see Table 1).

Example 3

(in accordance with the invention)

The same reactor as that of Example 1 was used, with the same operating conditions, and the same catalyst in an identical quantity, but the reactor contained three catalytic beds each separated by a SMV type static mixer sold by SULZER, immediately above which was a liquid distributor. Each static mixer was identical to that used in Example 2.

Under these conditions, conversion was 83%, the methane selectivity was 4%, and the selectivity towards $C_5^+$ hydrocarbons was 92% (see Table 1).

Example 4

(in accordance with the invention)

The same reactor as that of Example 1 was used, with the same operating conditions, and the same catalyst in an identical quantity, but the inlet conduit for the mixture of the synthesis gas and the liquid phase contained a SMV type static mixer sold by SULZER as described in Example 2 and between the fluid distributor and the catalyst bed, the reactor contained a static mixer which was identical to that included in the inlet conduit.

Under these conditions, conversion was 81%, the methane selectivity was 5%, and the selectivity towards $C_5^+$ hydrocarbons was 90% (see Table 1).

TABLE 1

| Examples | Conversion | $CH_4$ selectivity | $C_5^+$ selectivity |
|---|---|---|---|
| Ex 1 (comparative) 1 catalytic bed | 72% | 8% | 86% |
| Ex 2 | 78% | 6% | 88% |

TABLE 1-continued

| Examples | Conversion | $CH_4$ selectivity | $C_5^+$ selectivity |
|---|---|---|---|
| 2 catalytic beds + 1 mixer | | | |
| Ex 3 | 83% | 4% | 92% |
| 3 catalytic beds + 2 mixers | | | |
| Ex 4 | 81% | 5% | 90% |
| 2 mixers in reactor inlet conduit and reactor | | | |

Examples 2 to 4 show that, compared with the results of Example 1, the process of the invention can produce better selectivity towards $C_5^+$ hydrocarbons and a lower selectivity towards methane for higher degrees of conversion.

The process of the invention can thus:

mix the liquid phase(s) and the gas phase entering the reactor, when a mixer is located in the inlet conduit;

mix the liquid phase(s) and the gas phase in advance of the bed to ensure gas/liquid transfer to dissolve the hydrogen, so that a liquid composition with a high concentration of dissolved gas comes into contact with the active solid;

remix the liquid phase(s) and the gas phase from an upstream bed, which phases are separated to a greater or lesser extent and which can have differences in composition, before bringing them into contact with a downstream bed;

mix the synthesis gas and the liquid phase injected at said mixer with the liquid and gas phases formed during the reaction or present in the reactor;

distribute said mixture of phases homogeneously across the whole cross section of the bed, so that the concentrations of liquid and gas are uniformly distributed over the whole cross section of the bed;

and additionally, it can equalise the temperatures over the whole cross section.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

The entire disclosure of all applications, patents and publications, cited above and below, and of corresponding French application 96/02.911, are hereby incorporated by reference.

We claim:

1. A process for the synthesis of essentially linear saturated $C_5^+$ hydrocarbons from a gas phase comprising synthesis gas by the Fischer-Tropsch reaction which comprises circulating a liquid phase and said gas phase in a reaction zone, in which the reaction zone has at least one means for introducing gas and liquid phases, at least one means for extracting a hydrocarbon phase formed by the Fischer-Tropsch reaction, and at least one mixing means which is a static mixer positioned so that the liquid phase and gas phase are mixed thereby.

2. A process according to claim 1, in which at least one mixing means is also a means for distributing or redistributing the liquid and gas phases.

3. A process according to claim 1, in which at least one mixing means is associated with a means for distributing or redistributing the liquid and gas phases.

4. A process according to claim 1, in which at least one mixing means is located in the means for introducing the gas and liquid phases.

5. A process according to claim 1, in which the static mixer is composed of plates angled and arranged so as to form open channels which cross over, disposed obliquely with respect to the reaction zone axis.

6. A process according to claim 1, in which the reaction zone comprises at least one catalytic bed, and in which the liquid and gas phases circulate in the same direction, and wherein at least one catalytic bed is associated with at least one mixing means, located upstream of said catalytic bed, in the sense of the passage of said phases over said bed.

7. A process according to claim 6, wherein the reaction zone comprises multiple catalytic beds each catalytic bed being associated with at least one mixing means.

8. A process according to claim 7, in which at least one mixing means located between two catalytic beds is associated upstream with a means for collecting the liquid and gas phases and downstream with a means for redistributing the liquid and gas phases.

9. A process according to claim 8, in which at least one mixing means located between two catalytic beds is also a means for collecting liquid and gas phases arriving from upstream and a means for redistributing the liquid and gas phases in a downstream direction.

10. A process according to claim 9, in which at least one mixing means for collecting, mixing and redistributing fluids further comprises at least one means for introducing synthesis gas into the collected mixture.

11. A process according to claim 8, in which at least one static mixer comprises at least a portion of the catalyst present in the catalytic bed with which said mixer is associated.

12. A process according to claim 10, in which said mixer comprises the totality of the catalyst present in the catalytic bed with which said mixer is associated.

13. A process according to claim 1, in which the liquid phase is a hydrocarbon cut.

14. A process according to claim 13, in which said cut consists essentially of hydrocarbons containing 10 to 20 carbon atoms per molecule.

15. A process according to claim 1, in which the liquid phase is a gas oil fraction or a kerosene fraction.

16. A process according to claim 1, in which the liquid phase comprises at least one partially vaporizable product.

17. A process according to claim 1, in which the liquid phase comprises a hydrocarbon cut comprising hydrocarbons containing 5, 6, 7, 8, 9 or 10 carbon atoms per molecule.

18. A process according to claim 1, in which conversion of synthesis gas to hydrocarbons is carried out at a total pressure which is in the range 0.1 to 15 MPa, a temperature which is in the range 150° C. to 350° C., an hourly space velocity which is in the range 100 to 20000 volumes of synthesis gas per volume of catalyst per hour, and an $H_2$/CO molar ratio in the synthesis gas which is in the range 0.5 to 5.

19. A process according to claim 1, in which the catalyst is reduced in the reaction zone before the synthesis.

20. A process according to claim 1, in which the liquid phase is obtained by recycling a portion of a hydrocarbon fraction produced by the reaction.

21. The process of claim 1, wherein the reaction zone is in the form of a trickle bed reactor.

22. The process of claim 21, wherein the trickle bed reactor reaction zone contains a plurality of fixed beds each containing a catalyst for the Fischer-Tropsch reaction each separated from the other by at least one mixing means capable of collecting the liquid and gas phases leaving the fixed bed, mixing the collected phases and redistributing the mixture to a downstream fixed bed.

23. The process of claim 22, wherein each of the mixing means is a static mixer.

24. The process of claim 21, wherein at least one static mixer occupies the whole cross section of the reaction zone.

25. The process of claim 21, wherein at least one static mixer occupies a cross section of the reaction zone at least equal to the cross section occupied by a catalyst bed immediately upstream or downstream therefrom.

26. The process of claim 1, wherein the static mixer is in the form of multiple corrugated plates touching each other to form open intersecting channels.

* * * * *